(12) United States Patent
Eliasson

(10) Patent No.: US 7,826,588 B2
(45) Date of Patent: Nov. 2, 2010

(54) DEVICE AND METHOD TO GENERATE DIGITAL X-RAY IMAGES OF A SAMPLE

(75) Inventor: Eva Eliasson, Nusernberrz (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/397,407

(22) Filed: Mar. 4, 2009

(65) Prior Publication Data
US 2009/0225935 A1  Sep. 10, 2009

(30) Foreign Application Priority Data
Mar. 4, 2008  (DE) .................. 10 2008 012 394

(51) Int. Cl.
*A61B 6/04* (2006.01)
(52) U.S. Cl. .......................................... 378/37; 378/62
(58) Field of Classification Search .................. 378/37, 378/207, 145, 146, 62, 208
See application file for complete search history.

(56) References Cited

U.S. PATENT DOCUMENTS

2004/0101095 A1* 5/2004 Jing et al. ..................... 378/37

* cited by examiner

*Primary Examiner*—Hoon Song
(74) *Attorney, Agent, or Firm*—Schiff Hardin LLP

(57) ABSTRACT

In a device and an associated method, an x-ray source and a digital x-ray detector to generate digital x-ray images of an examination subject or of a sample. A partial region of the digital x-ray detector is used to generate an x-ray image of the sample. The examination subject thus remains in the device. This has the advantage that the sample can be examined while the examination subject, for example a female breast, remains in an unchanged position.

12 Claims, 1 Drawing Sheet

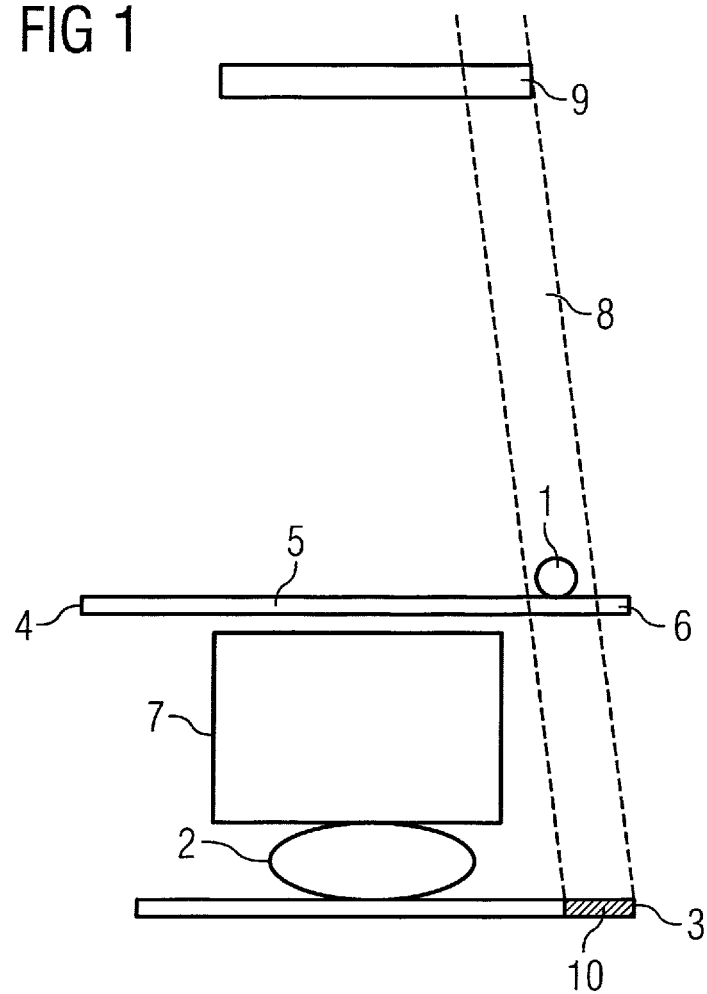
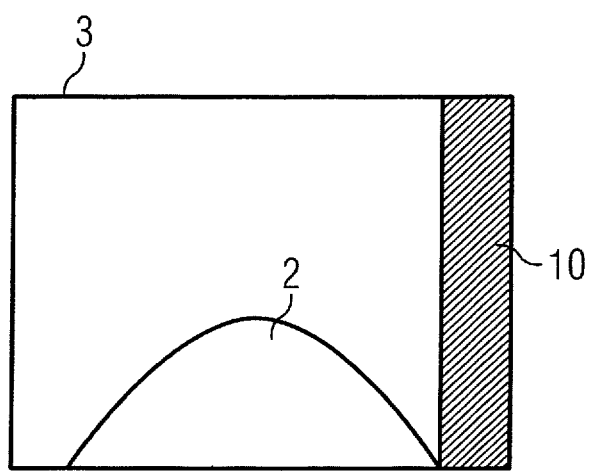

DEVICE AND METHOD TO GENERATE DIGITAL X-RAY IMAGES OF A SAMPLE

BACKGROUND OF THE INVENTION

1. Field of the Invention

The present invention concerns a device and an associated method for generation of a digital x-ray image of a sample.

2. Description of the Prior Art

X-ray image acquisitions of the human breast normally ensue with mammography apparatuses. Medical examinations of the soft tissue of the human breast that in particular serve for early detection of breast cancer can be conducted with x-ray radiation with a mammography apparatus. The breast to be examined is hereby clamped between a subject table and a compression plate that can be displaced against the subject table. An x-ray image acquisition subsequently ensues with a radiation unit fashioned as an x-ray receiver. For this an x-ray detector is typically integrated into the subject table. What is known as soft x-ray radiation in a range below 50 kV is used in the exposure.

Modern mammography apparatuses (for example the MAMMOMAT Novation" by the applicant) possess a base body fashioned as a stand and an angled apparatus arm projecting from the stand, on the free end of which apparatus arm is arranged a radiation source. The apparatus arm is realized as a plate construction and is connected in a rotationally fixed manner with a horizontal rotation axis of the mammography apparatus so that the radiation source can be pivoted by 360° around the isocenter.

The mammography apparatus is typically used for screening examinations in which the exposure unit is located in a 0° position in which the exposure unit and the subject table are arranged opposite one another in the longitudinal direction. Furthermore, the mammography apparatus is also fashioned for a stereo image examination in which the breast is exposed from two different angles, wherein here the exposure unit is pivoted from the rest position by +/−10° or, respectively, by +/−15° around the horizontal axis given a stationary subject table. Furthermore, examinations as tomosynthesis examinations are often also possible with the mammography apparatus, in which the exposure unit travels continuously over a comparably large angle range, for example in an angle range of +/−25° around the horizontal axis given a stationary subject table. Furthermore, an MLO (medio-lateral-oblique) depiction is typically possible. In this examination the exposure unit is normally located at a 45° position, wherein the subject table follows the exposure unit so that subject table and exposure unit are always aligned relative to one another in the same position and at the same distance. The mammography apparatus therefore allows the acquisition of the breast to be examined in standard depictions, for example what is known as the cranio-caudal (CC) or medio-lateral-oblique (MLO) depiction.

The "MAMMOMAT Novation", in cooperation with the digital biopsy and target acquisition system "Opdima" commercially available from Siemens Healthcare by the applicant, enables a stereotactic biopsy of the human breast. In stereotactic biopsy, a tissue sample of the human breast is extracted and subsequently histologically examined.

For the biopsy the breast is compressed in the mammography apparatus with a compression plate specially fashioned for the biopsy and is fixed in this position. A first x-ray image acquisition (what is known as the overview acquisition) subsequently ensues, via which it is checked whether the tumor or another tissue part to be biopsied lies within a recess of the compression plate.

All following acquisitions ensue in pairs from two different directions, as described above. They are therefore designated as stereo acquisitions. The point in the breast that is to be biopsied is marked from the first stereo acquisition, and from this the required entry position, entry direction and entry depth of a biopsy needles are calculated. The biopsy needle is subsequently inserted into the breast at the calculated point with the aid of a biopsy device, and additional stereo exposures are shot to monitor the position of the needle tip.

One or more samples are then extracted via the biopsy needle. In order to be able to establish whether the correct or, respectively, sufficient samples have been extracted, the samples are examined by means of x-rays. For this the patient must either leave the mammography apparatus so that the sample can be examined in the same apparatus, or an additional x-ray apparatus is provided for an x-ray image depiction of the sample. In the first case, the patient must be repositioned in the mammography apparatus for a possible follow-up examination and an additional biopsy, which entails an increased radiation exposure. In the second case, the stocking of an additional x-ray apparatus incurs additional costs.

SUMMARY OF THE INVENTION

An object of the invention is to provide an improved device and an associated method.

According to the invention, the device has an x-ray source and a digital x-ray detector to generate digital x-ray images of an examination subject or of a sample. A partial region of the digital x-ray detector is reserved to generate an x-ray image of the sample and is used for this. The examination subject remains in the device during the x-ray image acquisition of the sample.

It is advantageous for the sample to be examined while the examination subject (for example a female breast) remains in a compressed or, respectively, unchanged position.

In an embodiment, the device can comprise a biopsy unit and the sample can be obtained by means of the biopsy unit.

This has the advantage that the sample can be examined with the same mammography device during a stereotactic biopsy.

In an additional embodiment, the device can have a collimator with which the x-rays of the x-ray source on the sample can be delimited.

This prevents the x-ray radiation from radiating through regions that are not to be examined.

According to the invention, the device can have a support plate to bear the sample to be examined, so the region of the support plate that is not required for x-ray examination of the sample absorbs x-ray radiation.

The examination subject is thereby protected from unnecessary x-ray radiation.

In an embodiment, the partial region of the digital x-ray detector which is designed to generate an x-ray image of the sample can be fashioned as a boundary region of the digital x-ray detector.

This provides the advantage that the surface of the x-ray detector is optimally used.

According to the invention, a mammography device possesses the device according to the invention to generate digital x-ray images.

A stereotactic biopsy can thereby be used simply and efficiently in mammography.

According to the invention, a method is also specified to generate digital x-ray images of an examination subject or of a sample with a digital x-ray detector. A partial region of the digital x-ray detector is thereby used to generate an x-ray image of the sample while the examination subject remains in the device.

In an embodiment, the sample can be obtained by means of a biopsy unit.

In an additional embodiment, the x-rays of an x-ray source can be delimited or, respectively, concentrated on the sample with a collimator.

According to the invention, the sample to be examined can be borne on a support plate, wherein the region of the support plate that is not required for x-ray examination of the sample significantly absorbs x-ray radiation.

DESCRIPTION OF THE DRAWINGS

FIG. 1 is a side view of a mammography device.
FIG. 2 is a plan view of a digital x-ray detector.

DESCRIPTION OF THE PREFERRED EMBODIMENTS

FIG. 1 shows a mammography device according to the invention, with a digital x-ray detector 3 and an x-ray source (not shown) emitting x-ray radiation 8. A collimator 9 is set up so that the x-ray radiation 8 falls nearly exclusively on a region 6 of a support plate 4. The support plate 4 is arranged above a biopsy unit 7. The biopsy unit 7 itself is arranged above an examination subject 2 (for example a female breast) and compresses the subject 2. The examination subject 2 lies on the x-ray detector 3. The x-ray radiation 8 irradiates a sample 1 (which was obtained by means of the biopsy unit 7) arranged in a region 6 on the support plate 4. A digital x-ray image of the sample 1 irradiated by the x-ray radiation 8 is generated in the partial region 3 of the x-ray detector 10. To protect the examination subject 2 from unnecessary x-ray radiation 8, the support plate 4 is executed so as to strongly absorb x-ray radiation in the region 5. The support plate 4 is arranged such that it can pivot and can thus be introduced into or removed from the beam path of the x-ray source as needed.

The examination subject 2 remains in the mammography device during the x-ray acquisition of the sample 1. After the x-ray examination of the sample 1, the mammography or an additional biopsy can thus be continued without having to change the position of the examination subject 2.

A plan view of the digital x-ray detector 3 with an examination subject 2 supported on this is depicted in FIG. 2. the contour of the examination subject 2 (for example a female breast) and the partial region 10 of the x-ray detector that is provided for an x-ray image generation are shown. The x-rays (irradiating a sample (not shown in FIG. 2)) almost entirely strike this partial region 10. The partial region 10 is advantageously located at an edge of the x-ray detector 3.

Although modifications and changes may be suggested by those skilled in the art, it is the intention of the inventor to embody within the patent warranted hereon all changes and modifications as reasonably and properly come within the scope of her contribution to the art.

I claim as my invention:

1. An apparatus for generating digital x-ray images of an examination subject and of a sample excised from the examination subject, comprising:
   an x-ray source that emits x-rays;
   a digital x-ray detector disposed relative to said x-ray source to detect said x-rays emitted by said x-ray source;
   a support arrangement adapted to simultaneously support a subject and a sample excised from said subject and located outside of said subject;
   said x-ray source being configurable in a first configuration to irradiate said subject on said support arrangement, said digital x-ray detector detecting x-rays emitted from said x-ray source that are attenuated by said subject; and
   said x-ray source being configurable in a second configuration to irradiate only a portion of said digital x-ray detector, with said sample located between said x-ray source and the irradiated portion of the digital x-ray detector, to generate an x-ray image only of said sample on said support arrangement outside of said subject, without irradiating said subject, while said subject remains on said support arrangement between said x-ray source and said digital x-ray detector.

2. An apparatus as claimed in claim 1 comprising a biopsy unit that excises said sample.

3. An apparatus as claimed in claim 1 wherein said x-ray source comprises an x-ray emitter and a collimator that is attachable to and removable from said x-ray emitter, said collimator, when attached to said x-ray emitter, configuring said x-ray source in said second configuration to irradiate only said sample with said x-rays, and removal of said collimator configuring said x-ray source in said first configuration to irradiate said subject with said x-rays.

4. An apparatus as claimed in claim 1 comprising a support plate having a support plate region on which said sample is located when being irradiated with said x-rays, with a remainder of said support plate, outside of said support plate region, being comprised of x-ray absorbing material.

5. An apparatus as claimed in claim 1 wherein said x-ray source is configured in said second configuration to irradiate only an edge region of said digital x-ray detector to obtain said image only of said sample.

6. A mammography apparatus for generating digital x-ray images of a female breast and of a sample excised from the female breast, comprising:
   an x-ray source that emits x-rays;
   a digital x-ray detector disposed relative to said x-ray source to detect said x-rays emitted by said x-ray source;
   a support arrangement adapted to simultaneously support a female breast and a sample excised from said female breast and located outside of said female breast;
   said x-ray source being configurable in a first configuration to irradiate said female breast on said support arrangement, said digital x-ray detector detecting x-rays emitted from said x-ray source that are attenuated by said female breast;
   said x-ray source being configurable in a second configuration to irradiate only a portion of said digital x-ray detector, with said sample located between said x-ray source and the irradiated portion of the digital x-ray detector, to generate an x-ray image only of said sample on said support arrangement outside of said female breast, without irradiating said female breast, while said female breast remains on said support arrangement between said x-ray source and said digital x-ray detector; and
   said support arrangement comprising a compression plate adapted to compress the female breast during irradiation thereof by x-rays when said x-ray source is in said first configuration.

7. An mammography apparatus as claimed in claim 6 comprising a biopsy unit that excises said sample.

8. An mammography apparatus as claimed in claim 6 comprising a collimator that is attachable to and removable from said x-ray source, said collimator, when attached to said x-ray source, configuring said x-ray source to irradiate only said sample with said x-rays.

9. A method to generate a digital x-ray image of an examination subject and of a sample obtained from the subject, comprising the steps of:
- supporting a subject on a support arrangement between an x-ray source and a digital x-ray detector;
- excising a tissue sample from the subject and placing the tissue sample on the support arrangement outside of the subject;
- configuring the x-ray source in a first configuration and, in said first configuration, irradiating the subject on the support arrangement and detecting x-rays emitted by the x-ray source, and attenuated by the subject, with the digital x-ray detector;
- configuring the x-ray source in a second configuration to irradiate only a portion of the digital x-ray detector and, in said second configuration, irradiating only the sample with x-rays from said x-ray source, and detecting x-rays attenuated by said sample with said portion of said digital x-ray detector, while said subject remains on said support arrangement, without irradiating said subject on said support arrangement with x-rays emitted by said x-ray source.

10. A method as claimed in claim 9 comprising excising said tissue sample from said subject with a biopsy unit.

11. A method as claimed in claim 9 comprising configuring said x-ray source in said second configuration by collimating x-rays emitted by said x-ray source to cause said x-rays to irradiate only said sample while said subject remains between said x-ray source and said digital x-ray detector.

12. A method as claimed in claim 9 comprising supporting the subject on a support plate between said x-ray source and said digital x-ray detector, and placing said sample on said support plate in a support plate region when irradiating the tissue sample with said x-rays, and forming the support plate outside of said support plate region from x-ray absorbing material.

* * * * *